United States Patent [19]

de Nanteuil et al.

[11] Patent Number: 5,403,953

[45] Date of Patent: Apr. 4, 1995

[54] 1-PHENYLBICYCLO[2.2.2]OCTANE COMPOUNDS

[75] Inventors: Guillaume de Nanteuil, Suresnes; Michel Vincent, Bagneux; Christine Lila, Viroflay; Jacqueline Bonnet, Paris; Armel Fradin, Neuilly sur Seine, all of France

[73] Assignee: Adir et Compagnie, Courbevoie, France

[21] Appl. No.: 156,299

[22] Filed: Nov. 23, 1993

[30] Foreign Application Priority Data

Nov. 24, 1992 [FR] France ................... 92 14058

[51] Int. Cl.$^6$ ............................................. C07C 62/06
[52] U.S. Cl. ...................... 562/466; 562/427; 562/452; 562/455; 562/457; 562/467; 560/15; 560/38; 546/159; 546/168; 549/405; 549/425; 549/470; 558/404; 558/406; 564/162; 564/163; 564/164; 564/172; 564/180
[58] Field of Search ............... 562/466, 427, 452, 455, 562/457, 467; 560/15, 38; 546/159, 168; 549/405, 425, 470; 514/313, 456, 469, 532, 534, 538, 569; 558/404, 406; 564/162, 163, 164, 172, 180

[56] References Cited

U.S. PATENT DOCUMENTS 3,308,160 3/1967 Snyder .......................... 260/570.5
3,362,878 1/1968 Snyder .......................... 167/65

OTHER PUBLICATIONS

Craik, R. et al., Magn. Reson. Chem. (1986) 24(9) 783–91.
Adcock, W. et al J. Org. Chem. (1982) 47(15) 2945–51.
Kelly, S. et al., Helv. Chim. Acta (1984) 67(6) 1580–7.
Carr, N. et al. Mol. Cryst Lig. Cryst (1985) 130 (3-4) 265–79.

*Primary Examiner*—Paul J. Killos
*Attorney, Agent, or Firm*—Gordon W. Hueschen

[57] ABSTRACT

Compound of formula (I):

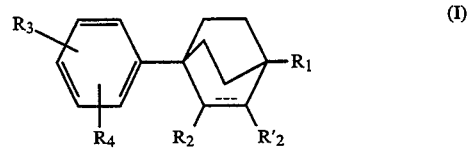

in which:

$R_1$ represents halogen, or hydroxy, alkyl, alkoxy, cyano, amino, mercapto, alkylthio or phenoxy, $R_2$ and $R'_2$ represent two hydrogen when the ring is unsaturated, or alternatively identical or different, represent hydrogen or halogen, or hydroxy, alkyl, alkoxy, cyano, amino or oxo when the ring is saturated, $R_3$ represents any one of the following groups:

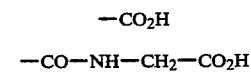

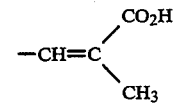

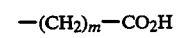

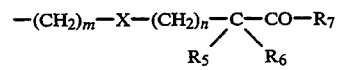

in which:

m represents 1, 2 or 3,

X represents oxygen or sulfur or N-R, $R_5$ or $R_6$, which are identical or different, represent hydrogen or alkyl or trifluoromethyl or form ($C_3$-$C_6$) cycloalkyl, n represents 0, 1 or 2, $R_7$ represents hydroxy, alkoxy, amino, or —O—CH$_2$—CO—NRR', $R_4$ represents hydrogen or halogen or alkyl, alkoxy or trihaloalkyl.

6 Claims, No Drawings

1-PHENYLBICYCLO[2.2.2]OCTANE COMPOUNDS

The present invention relates to new 1-phenylbicyclo[2.2.2]octane compounds.

These compounds, in addition to the fact that they are new, possess pharmacological properties which render them useable in the treatment of arthritis.

During the inflammatory reaction, substantial modifications occur in the synthesis of a group of plasma proteins called acute-phase proteins. Some of these proteins—including fibrinogen, reactive protein C, haptoglobin, amyloid serum A, $\alpha_2$-macroglobulin—are increased during the acute-phase reaction, whereas others such as albumin and transferrin are reduced. The alteration of these proteins, in particular fibrinogen, is responsible for the modifications in the plasma viscosity and in the speed of sedimentation which are observed in the inflammation. Because of their correlation with clinical parameters during the development and the therapeutic remissions observed in rheumatoid arthritis, some of these acute-phase proteins have been used as criterion for evaluating the disease (Mallya R K et al., J. Rheumatol., 1982, 9, 224-8; Thompson P W et al., Arthritis Rheum 1987, 30, 618-23). They are under the dependence of cytokines (Sipe J D, Interleukin 1 as a key factor in the acute-phase response. In: The acute-phase response to injury and infection. Edited by Gordon/Koj. Elsevier Science Publishers BV (Biomedical Division), 1985, p 23–35; Gauldie J et al., Cytokines and acute-phase protein expression. In: Cytokines and Inflammation. Edited by E S Kimball. CRC Press, 1991, p 275-305) which are recognized as playing an important role in arthritic pathology.

In animal pharmacology, the modifications of the acute-phase proteins have been studied, in particular, in rats during the acute inflammatory phase following the injection of complete adjuvant (Lewis E J et al., J. Pharmacol Meth 1989, 21, 183-94).

More specifically, the present invention relates to the compounds of formula (I):

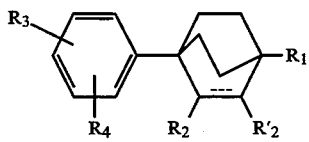

in which:

$R_1$ represents a halogen atom, a hydroxy group, a linear or branched ($C_1$-$C_6$) alkyl group (optionally substituted by one or more halogen atoms), a linear or branched ($C_1$-$C_6$) alkoxy group (optionally substituted by one or more halogen atoms), a cyano group, an amino group (unsubstituted or substituted by one or two linear or branched ($C_1$-$C_6$) alkyl groups), a mercapto group, a linear or branched ($C_1$-$C_6$) alkylthio group or a phenoxy group (unsubstituted or substituted by one or more halogen, hydroxy, linear or branched ($C_1$-$C_6$) alkyl, linear or branched ($C_1$-$C_6$) alkoxy or linear or branched ($C_1$-$C_6$) trihaloalkyl atoms or groups, which are identical or different), $R_2$ and $R'_2$ represent two hydrogen atoms in the case where the bicyclooctane ring is unsaturated, or alternatively $R_2$ or $R'_2$, in the case where the bicyclooctane ring is saturated, which are identical or different, represent a hydrogen or halogen atom, a hydroxy group, a linear or branched ($C_1$-$C_6$) alkyl group, a linear or branched ($C_1$-$C_6$) alkoxy group, a cyano group, an amino group (unsubstituted or substituted by one or two linear or branched ($C_1$-$C_6$) alkyl groups) or an oxo group, $R_3$ represents any one of the following groups:

—$CO_2H$ (on the condition that in this case, $R_1$ is different from a halogen atom, a linear ($C_1$-$C_6$) alkyl group or an amino group),

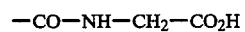

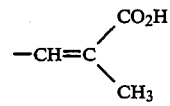

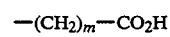

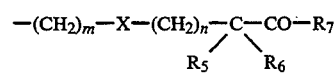

in which:

m represents 1, 2 or 3,

X represents an oxygen or sulfur atom or an N-R group (in which R is a hydrogen atom or a linear or branched ($C_1$-$C_6$) alkyl group), $R_5$ or $R_6$, which are identical or different, represent a hydrogen atom, a linear or branched ($C_1$-$C_6$) alkyl group, a trifluoromethyl group or

forms a ($C_3$-$C_6$) cycloalkyl radical, n represents 0, 1 or 2, $R_7$ represents a hydroxy group, a linear or branched ($C_1$-$C_6$) alkoxy group, an amino group (unsubstituted or substituted by one or two linear or branched ($C_1$-$C_6$) alkyl groups), a group —O—$CH_2$—CO—NRR' (such that R and R' represent a linear or branched ($C_1$-$C_6$) alkyl group, or form, with the nitrogen atom carrying them, a 5 or 6-membered heterocycle), or any one of the following heterocycles:

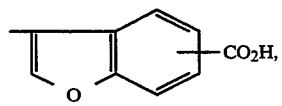

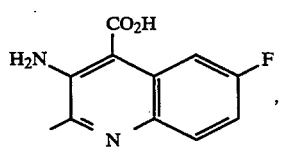

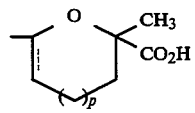

in which p is equal to 0 or 1

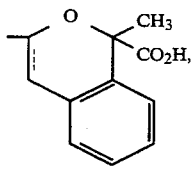

$R_4$ represents a hydrogen or halogen atom or a linear or branched ($C_1$–$C_6$) alkyl group, a linear or branched ($C_1$–$C_6$) alkoxy group or a ($C_1$–$C_6$) trihaloalkyl group, the dotted lines in the rings indicating the presence or otherwise of a double bond, their enantiomers, diastereoisomers, epimers as well as their addition salts with a pharmaceutically acceptable acid or base.

Among the pharmaceutically acceptable acids, there may be mentioned, with no limitation being implied, hydrochloric, sulfuric, tartaric, maleic, fumaric, methanesulfonic and camphoric acids and the like.

Among the pharmaceutically acceptable bases, there may be mentioned, with no limitation being implied, sodium hydroxide, potassium hydroxide, tert-butylamine., diethylamine, ethylenediamine and the like.

The invention also extends to the process for preparing the compounds of formula (I) characterized in that there is used as starting material a compound of formula (II):

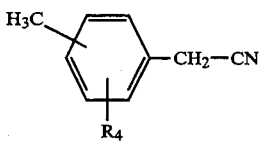
(II)

in which $R_4$ has the same meaning as in formula (I), which is reacted with methyl acrylate in the presence of a base to give the compound of formula (III):

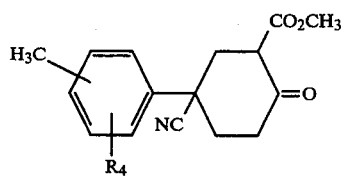
(III)

in which $R_4$ has the same meaning as in formula (I), which is subjected to the action of para-toluenesulfonic acid in ethylene glycol, to give a compound of formula (IV):

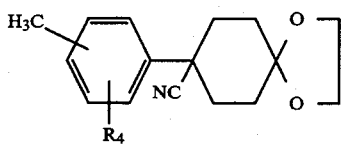
(IV)

in which $R_4$ has the same meaning as in formula (I), which is subjected to the action of methylmagnesium iodide, under an inert atmosphere, to give the compound of formula (V):

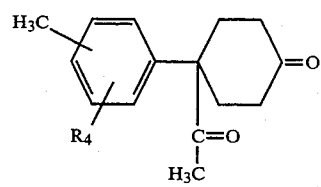
(V)

in which $R_4$ has the same meaning as in formula (I), which is reacted, in anhydrous medium, with an alcohol in acidic medium, to give the compound of formula (VI):

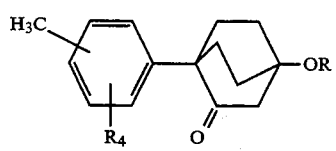
(VI)

in which $R_4$ has the same meaning as in formula (I) and R represents a linear or branched ($C_1$–$C_6$) alkyl group, which compound of formula (VI) is subjected to:

either a total reduction in the presence of hydrazine hydrate and a base to give the compound of formula (VIIa):

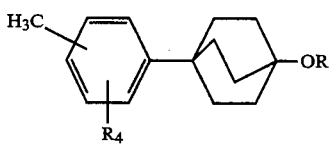
(VIIa)

in which $R_4$ and R have the same meaning as above, or a partial reduction in the presence of lithium aluminum hydride in ether, followed or otherwise by a dehydration to give respectively the compounds of formulae (VIIb) and (VIIc):

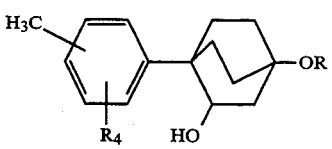
(VIIb)

(compound of formula (VIIb) whose hydroxy group is converted, if desired, to a halogen atom or to an alkoxy, amino or cyano group, according to conventional organic chemistry techniques),

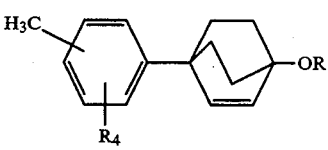
(VIIc)

in which $R_4$ and R have the same meaning as above, or the action of a phosphorus ylide followed by a reduction to give the alkylated compound of formula (VIId):

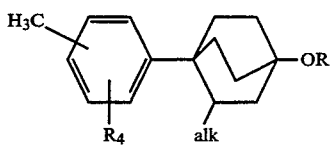 (VIId)

in which R₄ and R have the same meaning as above and alk means linear or branched ($C_1$-$C_6$) alkyl, or, after conversion to lithium enolate, an oxidation by means of MoOPH (oxodiperoxymolybdenum- pyridinehexamethylphosphoramide) to give the compound of formula (VIIe):

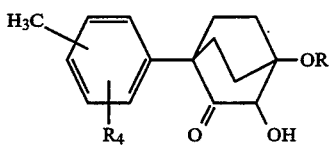 (VIIe)

in which R₄ and R have the same meaning as above (compound of formula (VIIe) whose hydroxy group is converted, if desired, to a halogen atom or to an alkoxy, amino or cyano group according to conventional organic chemistry techniques, which is then optionally reduced), which compounds of formula (VIIa) to (VIIe) (whose OR group is converted, if desired, to a hydroxy group or to a halogen atom and then to an amino, cyano, phenoxy, alkyl, mercapto or alkylthio group, according to conventional organic chemistry techniques), constitute the set of compounds of formula (VII):

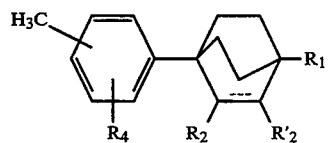 (VII)

in which $R_1$, $R_2$, $R'_2$ and $R_4$ have the same meaning as in formula (I), which are converted to the corresponding bromine- containing compound of formula (VIIIa) by the action of N-bromosuccinimide in inert medium:

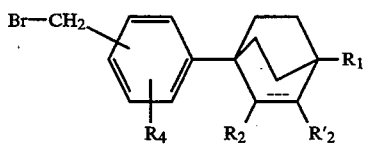 (VIIIa)

in which $R_1$, $R_2$, $R'_2$ and $R_4$ have the same meaning as in formula which compound of formula (VIIIa), whose —CH₂Br group is optionally converted to a corresponding —CH₂CN group and then to a —CH₂CO₂H group, may again be subjected to conventional organic chemistry reactions giving:

the compound of formula (I/a), which is a specific example of the compounds of formula (I):

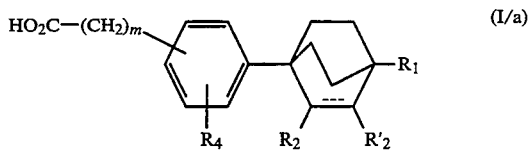 (I/a)

in which $R_1$, $R_4$, $R_2$, $R'_2$ and m have the same meaning as in formula (I), or the compound of formula (VIIIb):

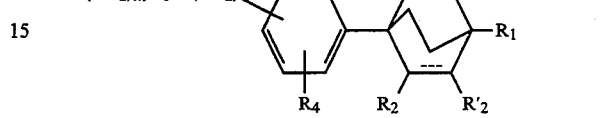 (VIIIb)

in which $R_1$, $R_2$, $R'_2$, $R_4$ and m have the same meaning as in formula (I), which compound of formula (VIIIa) or (VIIIb) is reacted:

a with a compound of formula (IX):

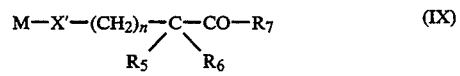 (IX)

in which M represents an alkali metal, n, $R_5$, $R_6$ and $R_7$ are as defined in formula (I) and X' represents a sulfur or oxygen atom, to give the compound of formula (I/b), which is a specific example of the compounds of formula (I):

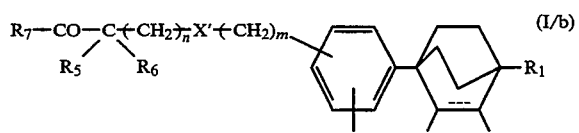 (I/b)

in which $R_5$, $R_6$, $R_7$, m, n, X', $R_4$, $R_2$, $R'_2$ and $R_1$ have the same meaning as above, whose $R_7$, when it represents a hydroxy group, is converted, if desired, to the corresponding amino or ester group according to conventional techniques for converting an acid functional group to an amide functional group, b with hexamethylenetetramine in chloroformic medium, then in acetic medium, to give respectively the aldehydes of formula (Xa) or (Xb):

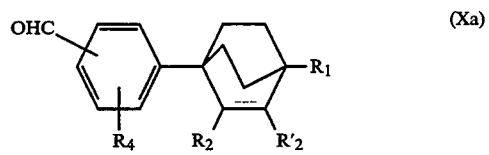 (Xa)

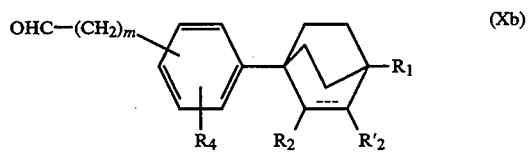 (Xb)

which compound of formula (Xa) is subjected to:
* either the action of an oxidant such as silver nitrate, to give the compound of formula (I/c), which is a specific example of the compounds of formula (I):

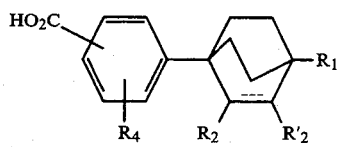

(I/c)

in which $R_1$, $R_4$, $R_2$ and $R'_2$ have the same meaning as above, which may be optionally reacted:

after conversion to the acid chloride, with the phosphorus ylide of formula (XI):

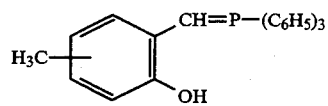

(XI)

to give the compound of formula (XII):

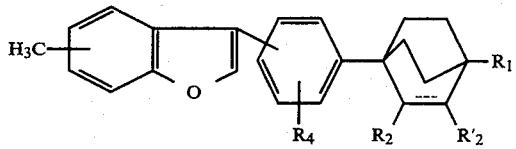

(XII)

in which $R_1$, $R_4$, $R_2$ and $R'_2$ have the same meaning as above, which is converted to the compound of formula (I/d), which is a specific example of the compounds of formula (I), according to the same reactions as those described for passing from the compound of formula (VII) to the compound of formula (I/c) via the compounds of formulae (VIIIa) and (Xa):

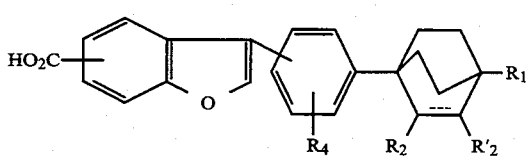

(I/d)

in which $R_1$, $R_2$, $R'_2$ and $R_4$ have the same meaning as above, after conversion to the acid chloride, with diazomethane to give the corresponding diazomethyl ketone which is converted to bromomethyl ketone and then to aminomethyl ketone to give, after reacting with 5-fluoroisatin, the compound of formula (I/e), which is a specific example of the compounds of formula (I):

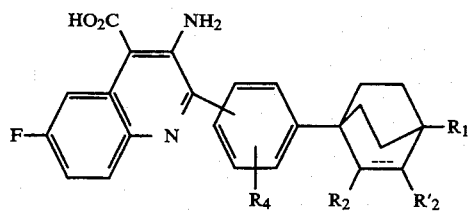

(I/e)

in which $R_1$, $R_2$, $R'_2$ and $R_4$ have the same meaning as in formula (I), or, with the methyl ester of glycine according to the conventional peptide coupling technique described by W. KÖNIG and R. GEIGER (Chem. Ber., 103., 788, 2024, 1970), to give the compound of formula (I/f), which is a specific example of the compounds of formula (I):

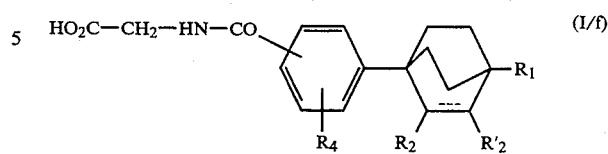

(I/f)

in which $R_1$, $R_2$, $R'_2$ and $R_4$ have the same meaning as in formula (I),

* or the action of the magnesium compound $C_6H_5CH_2MgBr$ followed or otherwise by an oxidation reaction, then that of methyl pyruvate in acidic medium, to give, after saponification, the compound of formula (I/g), which is a specific example of the compounds of formula (I):

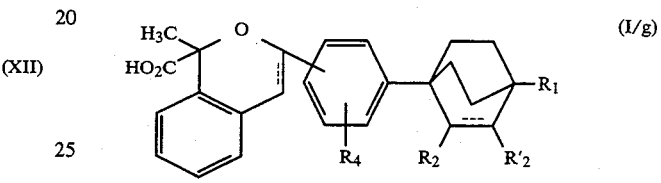

(I/g)

in which $R_1$, $R_2$, $R'_2$ and $R_4$ have the same meaning as in formula

* or the action of the magnesium compound $CH_2=CH-MgBr$ followed or otherwise by an oxidation reaction, then that of methyl pyruvate in acidic medium, to give, after saponification, the compound of formula (I/h), which is a specific example of the compounds of formula (I):

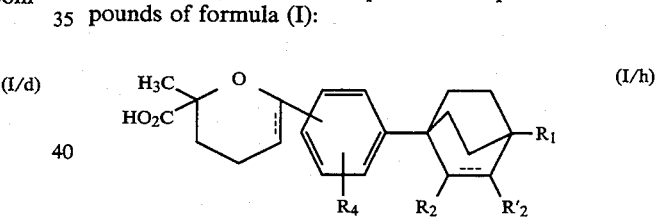

(I/h)

in which $R_1$, $R_2$, $R'_2$ and $R_4$ have the same meaning as in formula (I),

* or the action of:

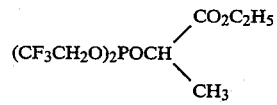

in the presence of a base, to give, after saponification, the compound of formula (I/i):

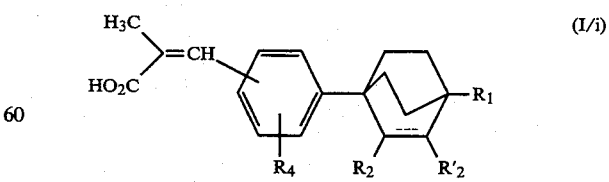

(I/i)

in which $R_1$, $R_2$, $R'_2$ and $R_4$ have the same meaning as in formula (I), which compounds of formula (Xa) or (Xb), may be subjected to the action of an amino ester of formula (XIII):

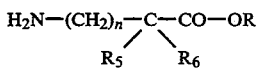

in which R represents an alkyl group, n, $R_5$ and $R_6$ have the same meaning as above, to give the compound of formula (I/j), which is a specific example of the compounds of formula (I):

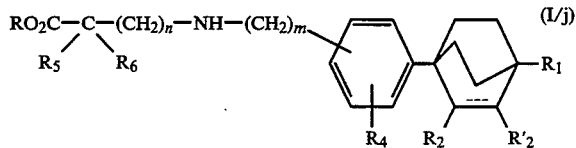

compound of formula (I/j) whose corresponding acid functional group or amide functional group is converted, if desired, according to conventional organic chemistry techniques and whose secondary amine functional group is converted, if desired, to a tertiary amine functional group by alkylation, which compounds of formula (I/a), (I/b), (I/c), (I/d), (I/e), (I/f), (I/g), (I/h), (I/i) or (I/j) are purified, where appropriate, according to a conventional purification technique, whose isomers are separated, if desired, according to conventional separation techniques, and which are optionally converted to their addition salts with a pharmaceutically acceptable acid or base.

These new 1-phenylbicyclo[2.2.2]octane compounds have very useful pharmacological properties. They reduce the effects of an injection of Freund's adjuvant in rats both at the level of the acute phase plasma proteins (albumin) and the acute edema itself, while preventing, at a later stage, the onset of polyarthritis. This effect indicates an anti-inflammatory activity of the compounds of the invention.

The invention also extends to the pharmaceutical compositions containing, as active ingredient, at least one compound of formula (I) or its optical isomers with one or more inert, nontoxic and appropriate excipients. The pharmaceutical compositions thus obtained can be provided in various forms, the most advantageous being tablets, sugar-coated tablets, hard gelatin capsules, suppositories, suspensions to be taken orally, the transdermal forms (gel, patch), and the like. The useful dosage can be adjusted according to the nature and severity of the condition, the route of administration as well as according to the age and the weight of the patient. This unit dosage ranges from 0.02 g to 2 g per day in one or more doses.

The following examples illustrate the invention but do not limit it in any manner.

EXAMPLE 1:
2-Methyl-2-{[3-(4-methoxybicyclo[2.2.2]oct-1-yl)phenyl]methoxy}propionic acid, sodium salt

Stage A:
2-Methoxycarbonyl-4-cyano-4-(3-methylphenyl)cyclohexan-1-one 190 mmol of m-tolylacetonitrile are added to 64 ml of a methanolic solution containing 198 mmol of sodium methoxide, then dropwise 380 mmol of methyl acrylate. The mixture is refluxed for 3 hours. After hydrolysis with 200 ml of 1N hydrochloric acid, extraction with ethyl acetate and then washing with water and evaporation, the expected product is purified by silica column chromatography, using as eluent a dichloromethane/ethyl acetate mixture (95/5).

Stage B:
8-(3-Methylphenyl)-8-cyano-1,4-dioxaspiro[4.5]decane

A mixture containing 73 mmol of the product obtained in the preceding stage, 1.07 g of para-toluenesulfonic acid, 11 ml of water and 110 ml of ethylene glycol is refluxed for 4 hours. After returning to room temperature, hydrolysis with 150 ml of a saturated aqueous solution of ammonium chloride, extraction with ether, washing, the expected product is obtained in the form of an oil after silica column purification, using as eluent a pentane/ethyl acetate mixture (8/2).

Stage C: 4-Acetyl-4-(3-methylphenyl)cyclohexan-1-one 145 ml of a 3M methylmagnesium iodide solution in ether are placed in 100 ml of anhydrous tetrahydrofuran, under a nitrogen atmosphere. The mixture is heated to 50° C. and then 144 mmol of the product obtained in the preceding stage, in solution in 100 ml of THF, are slowly added. The mixture is refluxed for 24 hours. After hydrolysis with 60 ml of concentrated hydrochloric acid and 150 ml of water, the medium is refluxed for 12 hours. After returning to room temperature, extraction with ethyl acetate, washing and evaporation, the expected product is purified by silica column chromatography, using as eluent a dichloromethane/ethyl acetate mixture (97.5/2.5).

Stage D: 2-Oxo-4-methoxy-1-(3-methylphenyl)bicyclo[2.2.2]octane

A stream of hydrochloric acid is passed over a solution, at 0° C., containing 112 mmol of the compound obtained in the preceding stage, in 150 ml of anhydrous methanol, for 3 hours. The mixture is kept stirring at room temperature for 12 hours. After evaporation of the solvent, the mixture is taken up in ethyl acetate, evaporated, dried and the expected product is obtained after silica column purification, using as eluent a pentane/ethyl acetate mixture (9/1).

Stage E:
1-(3-Methylphenyl)-4-methoxybicyclo[2.2.2]octane 29 mmol of the product obtained in the preceding stage, in solution in 35 ml of hydrazine hydrate, are heated for 5 hours at 160° C. After addition of 8 g of potassium hydroxide and 50 ml of ethylene glycol, the mixture is heated for one hour at 160° C. and then at 220° C. until the evolution of nitrogen ceases. After returning to room temperature, the mixture is poured over 100 ml of water and extracted with ether. After washing, drying and evaporation, the expected product is obtained.

Stage F:
1-Methoxy-4-(3-bromomethylphenyl)bicyclo[2.2.2]octane 27 mmol of the compound obtained in the preceding stage are placed in 130 ml of anhydrous carbon tetrachloride. After addition of one equivalent of N-bromosuccinimide and then 0.1 equivalent of AIBN, the mixture is refluxed for 2 hours. After returning to room temperature and then cooling, the mixture is filtered and rinsed. The filtrate is evaporated and gives the expected product.

Stage G: Ethyl 2-methyl-2-{[3-(4-methoxybicyclo[2.2.2]oct-1-yl)phenyl]methoxy}propionate 37.6 mmol of sodium hydride are placed in 33 mmol of anhydrous dimethylformamide under a nitrogen atmosphere. 37.6 mmol of ethyl 2-hydroxyisobutyrate, in 16 ml of DMF, are then added dropwise. The mixture is left stirring for one hour and then cooled to 0° C. 27 mmol of the compound obtained in the preceding stage, in 20 ml of DMF, are then added and the mixture is allowed to stand for 12 hours at room temperature. 15 ml of a saturated ammonium chloride solution are then added at 5° C. After evaporation of the DMF, taken up in 200 ml of ethyl acetate and 100 ml of water, the organic phase is extracted, dried and evaporated. The expected product is then obtained after silica column purification, using as solvent a pentane/ethyl acetate mixture (90/10).

Elemental microanalysis:

|  | C % | H % |
| --- | --- | --- |
| calculated | 73.30 | 8.95 |
| found | 73.42 | 8.79 |

Stage H: 2-Methyl-2-{[3-(4-methoxybicyclo[2.2.2]oct-1-yl)phenyl]methoxy}propionic acid, sodium salt 8 mmol of sodium hydroxide pellets and then 4 ml of water are added to a solution containing 8 mmol of the product obtained in the preceding stage, in 60 ml of ethanol. The mixture is refluxed for 3 hours. After evaporation, taking up the residue in water, extraction with ether, acidification with 4N hydrochloric acid, the expected product is obtained after filtration and drying and is converted to the corresponding sodium salt.

Elemental microanalysis:

|  | C % | H % |
| --- | --- | --- |
| calculated | 67.78 | 7.68 |
| found | 68.06 | 7.38 |

The compounds of Examples 2 and 3 were synthesized according to the same procedure as that described for Example 1, using the corresponding starting materials.

EXAMPLE 2: 2-Methyl-2-{[4-(4-methoxybicyclo[2.2.2]oct-1-yl)phenyl]methoxy}propionic acid, sodium salt Elemental microanalysis:

|  | C % | H % |
| --- | --- | --- |
| calculated | 67.78 | 7.68 |
| found | 67.65 | 7.37 |

EXAMPLE 3: 2-Methyl-2-{[4-(4-ethoxybicyclo[2.2.2]oct-1-yl)phenyl]methoxy}propionic acid, sodium salt Elemental microanalysis:

|  | C % | H % |
| --- | --- | --- |
| calculated | 68.46 | 7.93 |
| found | 68.47 | 7.50 |

EXAMPLE 4: Ethyl 2-methyl-2-{[4-(4-methoxybicyclo[2.2.2]oct-1-yl)phenyl]methoxy}propionate This compound was obtained by esterification, in ethanolic medium, of the compound described in Example 2.

Melting point: 52° C.

Elemental microanalysis:

|  | C % | H % |
| --- | --- | --- |
| calculated | 73.30 | 8.95 |
| found | 73.40 | 8.31 |

EXAMPLE 5: 2-Methyl-2-{[4-(4-chlorobicyclo[2.2.2]oct-1-yl)phenyl]methoxy}propionic acid, sodium salt Stages A, B, C, D and E are identical to Stages A, B, C, D and E of Example 2.

Stage F: 1-(4-Methylphenyl)-4-hydroxybicyclo[2.2.2]octane 5 mmmol of the product obtained in the preceding stage are heated at the reflux temperature of a solution containing 16 ml of dioxane and 16 ml of concentrated hydrochloric acid for 24 hours. After evaporation, the expected product is obtained after washing with water and drying.

Melting point: 144° C.

Stage G: 1-(4-Methylphenyl)-4-chlorobicyclo[2.2.2]octane 4.6 mmol of the compound obtained in the preceding stage are placed, in 10 ml of 1,2-dichloroethane, in contact with 9.2 mmol of thionyl chloride. The mixture is refluxed for 4 hours, evaporated and taken up in sodium bicarbonate and ethyl acetate. After extraction of the organic phase, washing, drying and evaporation, the expected product is obtained in the form of white crystals.

Melting point: 105° C.

Stages H, I and J

These stages are carried out according to the procedures described in stages F, G and H of Example 1 and give the title product.

Elemental microanalysis:

|  | C % | H % | Cl % |
| --- | --- | --- | --- |
| calculated | 63.60 | 6.74 | 9.88 |
| found | 63.41 | 6.59 | 9.97 |

EXAMPLE 6: Ethyl 2-([4-(4-chlorobicyclo[2.2.2]oct-1-yl)phenyl]methoxy}propionate This compound was obtained by esterification, in ethanolic medium of the compound of Example 5.

Elemental microanalysis:

|  | C % | H % | Cl % |
|---|---|---|---|
| calculated | 69.12 | 8.01 | 9.72 |
| found | 68.84 | 7.91 | 9.73 |

EXAMPLE 7:
2-Methyl-2-{[4-(4-methoxybicyclo[2.2.2]oct-1-yl)phenyl]methoxy}propionamide

Stage A:
2-Methyl-2-{[4-(4-methoxybicyclo[2.2.2]oct-1-yl)phenyl]methoxy}propionic acid chloride 4.7 mmol of the acid described in Example 2 are placed, in 10 ml of anhydrous dichloromethane, in contact with a few drops of dimethylformamide. The mixture is cooled to 0° C. and 33 mmol of oxalyl chloride are poured dropwise over this mixture. After stirring for 10 hours at room temperature, the expected product is obtained after evaporation.

Stage B:
2-Methyl-2-{[4-(4-methoxybicyclo[2.2.2]oct-1-yl)phenyl]methoxy}propionamide 4.7 mmol of the product obtained in the preceding stage are dissolved in 4 ml of dichloromethane and placed in 15 ml of a 28% ammoniacal solution and the mixture is stirred for 3 hours at room temperature. The expected product is obtained by filtration of the precipitate formed and drying.
Melting point: 186° C.
Elemental microanalysis:

|  | C % | H % | N % |
|---|---|---|---|
| calculated | 72.47 | 8.82 | 4.23 |
| found | 71.98 | 8.48 | 4.43 |

EXAMPLE 8:
[4-(4-Hydroxybicyclo[2.2.2]oct-1-yl)phenyl]acetic acid, sodium salt Stages A to F These stages are identical to Stages A to F of Example 2.

Stage G: 1-Methoxy-4-(4-cyanomethylphenyl)bicyclo[2.2.2]octane 6.8 mmol of sodium cyanide, in solution in 18 ml of water, are added to 5.7 mmol of the product obtained in the preceding stage, in 130 ml of acetonitrile. The mixture is refluxed for 2 hours. The expected product is obtained after evaporation of the acetonitrile, taken up in a water-ether mixture, extraction, drying and evaporation.

Stage H:
[4-(4-Hydroxybicyclo[2.2.2]oct-1-yl)phenyl]acetic acid, sodium salt 18 ml of concentrated hydrochloric acid are added dropwise to 5 mmol of the compound obtained in the preceding stage, in 18 ml of dioxane. The mixture is refluxed for 3 hours. The precipitate formed is filtered, washed with water and dried and is converted to the corresponding sodium salt.
Elemental microanalysis:

|  | C % | H % |
|---|---|---|
| calculated | 68.07 | 6.78 |
| found | 68.33 | 6.63 |

EXAMPLE 9:
4-(4-Methoxybicyclo[2.2.2]oct-1-yl)benzoic acid, sodium salt

Stages A to F
these stages are identical to Stages A to F of Example 2.

Stage G:
N-[4-(4-methoxybicyclo[2.2.2]oct-1-yl)benzyl]hexamethylenetetramonium bromide 68 mmol of hexamethylenetetramine are dissolved, under reflux, in 100 ml of chloroform. 68 mmol of the compound obtained in the preceding stage, in solution in 30 ml of chloroform, are then added. The mixture is maintained for 4 hours under reflux and the expected product is obtained in the form of a precipitate which is filtered and dried.

Stage H: 4-(4-Methoxybicyclo[2.2.2]oct-1-yl)benzaldehyde 15 mmol of the compound obtained in the preceding stage are placed in 44 ml of an acetic acid/water solution (1/1). The mixture is heated for 3 hours at 100° C. 10 ml of 6N hydrochloric acid are then added and the stirring is continued for 30 minutes. After returning to room temperature, the expected product is obtained after extraction with ether and purified by silica column chromatography, using as eluent a pentane/ethyl acetate mixture (9/1).
Elemental microanalysis:

|  | C % | H % |
|---|---|---|
| calculated | 78.65 | 8.25 |
| found | 78.87 | 8.40 |

Stage I: 4-(4-Methoxybicyclo[2.2.2]oct-1-yl)benzoic acid, sodium salt

Away from light, 46 mmol of sodium hydroxide, in 5 ml of water, are cooled to 0° C., then a solution containing 21 mmol of silver nitrate in 5 ml of water are added. 8.2 mmol of the product obtained in the preceding stage are then slowly added. The mixture is kept stirring for 10 hours. After filtration, washing with hot water and cooling of the filtrate, the expected product, in the form of free acid, is obtained by precipitation by means of 4N hydrochloric acid and filtration and is converted to the corresponding sodium salt.
Elemental microanalysis:

|  | C % | H % |
|---|---|---|
| calculated | 68.07 | 6.78 |
| found | 67.67 | 6.39 |

EXAMPLE 10:
2-Methyl-2-{[4-(2-hydroxy-4-methoxybicyclo[2.2.2]oct-1-yl)phenyl]methoxy}propionic acid, sodium salt

Stages A to D these stages are identical to Stages A to D of Example 2.

Stage E:
1-Methoxy-3-hydroxy-4-(4-methylphenyl)bicyclo[2.2.2]octane 8.2 mmol of the compound obtained in the preceding stage, in solution in 10 ml of anhydrous tetrahydrofuran, are added dropwise to a suspension, at 5° C., containing 10.6 mmol of $LiAlH_4$ in 20 ml of anhydrous THF. After one hour at 5° C., then 2 hours at room temperature, the mixture is again cooled to 5° C. and then hydrolysed. After filtration and evaporation of the filtrate, the residue is taken up in ether and water and extracted with ether and gives the expected product.

Elemental microanalysis:

|  | C % | H % |
|---|---|---|
| calculated | 78.01 | 9.00 |
| found | 78.05 | 8.85 |

Stage F: 1-Methoxy-2-acetyloxy-4-(4-methylphenyl)bicyclo[2.2.2]octane 7.5 mmol of the compound obtained in the preceding stage, in solution in 20 ml of chloroform, are acetylated in the presence of 1.1 equivalent of acetyl chloride and 1.1 equivalent of pyridine. The expected product is then obtained after evaporation and extraction with ether.

Elemental microanalysis:

|  | C % | H % |
|---|---|---|
| calculated | 74.97 | 8.39 |
| found | 75.19 | 8.18 |

Stages G to I these stages are identical to Stages F to H of Example 2

Elemental microanalysis:

|  | C % | H % |
|---|---|---|
| calculated | 64.85 | 7.35 |
| found | 64.55 | 6.94 |

Examples 11 and 12 were synthesized according to the same procedure as that described for Example 1, using the corresponding starting materials.

EXAMPLE 11:
{2-Methyl-2-[[4-(4-methoxybicyclo[2.2.2]oct-1-yl)phenyl]methoxy]propionyloxy}-N,N-diethylacetamide Melting point: 94° C.
Elemental microanalysis:

|  | C % | H % | N % |
|---|---|---|---|
| calculated | 70.08 | 8.82 | 3.14 |
| found | 70.22 | 8.78 | 3.51 |

EXAMPLE 12:
{2-Methyl-2-[[3-(4-methoxybicyclo[2.2.2]oct-1-yl)phenyl]methoxy]propionyloxy}-N,N-diethylacetamide Melting point: 84° C.
Elemental microanalysis:

|  | C % | H % | N % |
|---|---|---|---|
| calculated | 70.08 | 8.82 | 3.14 |
| found | 69.53 | 8.71 | 3.31 |

EXAMPLE 13:
2-Methyl-2-{[4-(4-methoxybicyclo[2.2.2]octo-1-yl)phenyl]methylamino}propionic acid, sodium salt Stages A to H are identical to Stages A to H of Example 9.

Stage I: Ethyl 2-methyl-2-{[4-(4-methoxybicyclo[2.2.2]oct-1-yl)phenyl]methylamino}propionate 22 g of molecular sieve (3 Å), 8.6 mmol of triethylamine and then 7.8 mmol of the compound obtained in the preceding stage, in solution in 30 ml of ethanol, are added to 7 mmol of ethyl 2-amino-2-methylpropionate in solution in 30 ml of ethanol. The mixture is kept stirring for 90 minutes, then 1.3 ml of acetic acid and 1 equivalent of sodium cyanoborohydride are added and the stirring is continued for 17 hours. The molecular sieve is filtered, rinsed with ether and the filtrate is evaporated. The residue is taken up in water and extracted with ethyl acetate. The expected product is obtained after purification by silica gel chromatography, using as eluent a dichloromethane/ethyl acetate mixture (70/30).

Elemental microanalysis:

|  | C % | H % |
|---|---|---|
| calculated | 69.55 | 7.30 |
| found | 69.82 | 7.25 |

Stage J:
2-Methyl-2-{[4-(4-methoxybicyclo[2.2.2]oct-1-yl)phenyl]methylamino}propionic acid, sodium salt The ester obtained in the preceding stage is saponified in ethanolic medium and then converted to the corresponding sodium salt.

Elemental microanalysis:

|  | C % | H % | N % |
|---|---|---|---|
| calculated | 67.97 | 7.99 | 3.96 |
| found | 67.93 | 7.48 | 3.97 |

EXAMPLE 14: 2-[4-(4-Methoxybicyclo[2.2.2]oct-1-yl)phenyl]benzofuran-7-carboxylic acid, sodium salt Stage A: 6-Methyl-2-hydroxymethylphenol 4.9 mmol of lithium aluminum hydride are placed, under a nitrogen atmosphere, in 50 ml of ether. 3.3 mmol of 2-hydroxy-3-methylbenzoic acid, in solution in 40 ml of ether, are added dropwise while maintaining a reflux for 4 hours. The mixture is then cooled on ice and 12.5 ml of isopropanol and then 7.5 ml of a saturated sodium chloride solution are added. After 10 hours at room temperature, the mixture is filtered, rinsed with 1N hydrochloric acid and extracted with ether. The product is then obtained after silica column purification, using as eluent a pentane/ethyl acetate mixture (7/3).

Elemental microanalysis:

|  | C % | H % |
| --- | --- | --- |
| calculated | 69.55 | 7.30 |
| found | 69.82 | 7.25 |

Stage B: 3-Methyl-2-hydroxybenzylphosphonium bromide 10 mmol of the product obtained in the preceding stage and 10 mmol of triphenylphosphonium bromide, in 10 ml of acetonitrile, are heated at 100° C. for 2 hours. The expected product precipitates, it is filtered, rinsed with ethyl acetate and dried.

Elemental microanalysis:

|  | C % | H % | Br % |
| --- | --- | --- | --- |
| calculated | 67.40 | 5.22 | 17.24 |
| found | 67.58 | 5.14 | 17.70 |

Stage C: 7-Methyl-2-[4-(4-methoxybicyclo[2.2.2]oct-1-yl)phenyl]benzofuran 31.4 mmol of the compound obtained in the preceding stage and 13.2 ml of triethylamine are added to 37 mmol of the chloride of the acid described in Example 9 (obtained by reaction of phosphorus pentachloride with the compound of Example 9) in solution in 120 ml of toluene. The mixture is refluxed for 8 hours. After filtration, the filtrate is evaporated, taken up in ethanol and gives the expected product by evaporation. Stages D to G are carried out using the same procedures as those described in Stages F to I of Example 9.

Elemental microanalysis:

|  | C % | H % |
| --- | --- | --- |
| calculated | 72.35 | 5.82 |
| found | 71.62 | 5.55 |

EXAMPLE 15: 1-{[4-(4-Methoxybicyclo[2.2.2]oct-1-yl)phenyl]methylamino}cyclopropanecarboxylic acid This compound was obtained according to the same procedure as that described in Example 13.

Elemental microanalysis:

|  | C % | H % | N % |
| --- | --- | --- | --- |
| calculated | 68.36 | 7.46 | 3.99 |
| found | 68.20 | 6.96 | 4.20 |

EXAMPLE 16: 2-Methyl-2-{[4-(4-methoxybicyclo[2.2.2]oct-1-yl)phenyl]methoxy}butanoic acid, sodium salt This compound was obtained according to the procedure described in Example 1.

Elemental microanalysis:

|  | C % | H % |
| --- | --- | --- |
| calculated | 68.46 | 7.93 |
| found | 68.95 | 7.64 |

EXAMPLE 17: 2-Methyl-2-{[4-(4-hydroxybicyclo[2.2.2]oct-1-yl)phenyl]methoxy}propionic acid, sodium salt Stages A to F are identical to Stages A to F of Example 5.

Stage G: 1-(4-Bromomethylphenyl)-4-hydroxybicyclo-[2.2.2]octane

The expected product is obtained according to the procedure described in Stage F of Example 1 from the 1-(4-methylphenyl)-4-hydroxybicyclo[2.2.2]octane obtained in the preceding stage.

Stages H and I these stages are carried out according to the procedures described in Stages G and H of Example 1 and give the title product.

Elemental microanalysis:

|  | C % | H % |
| --- | --- | --- |
| calculated | 67.04 | 7.40 |
| found | 67.35 | 7.09 |

EXAMPLE 18: 2-Methyl-2-{[4-(4-isopropyloxybicyclo[2.2.2]oct-1-yl)phenyl]methoxy}propionic acid, sodium salt This compound was obtained according to the procedure described in Example 1, from the corresponding starting materials.

Elemental microanalysis:

|  | C % | H % |
| --- | --- | --- |
| calculated | 69.09 | 8.17 |
| found | 69.03 | 7.96 |

EXAMPLE 19: 2-Methyl-2-{[4-(4-methoxybicyclo[2.2.2]oct-1-yl)phenyl]methoxy}propionic acid This compound was obtained by displacement, in hydrochloric medium, of the corresponding sodium salt described in Example 2.

Melting point: 169°–170° C.

Elemental microanalysis:

|  | C % | H % |
|---|---|---|
| calculated | 72.26 | 8.49 |
| found | 71.70 | 8.27 |

EXAMPLE 20:
2-Ethyl-2-{[4-(4-methoxybicyclo[2.2.2]oct-1-yl)phenyl]methoxy}butyric acid, sodium salt This compound was obtained according to the procedure described in Example 1, from the corresponding starting materials.

Elemental microanalysis:

|  | C % | H % |
|---|---|---|
| calculated | 69.09 | 8.17 |
| found | 69.46 | 8.12 |

EXAMPLE 21:
2-{[4-(4-Methoxybicyclo[2.2.2]oct-1-yl)phenyl)methoxy}propionic acid, sodium salt This compound was obtained according to the procedure described in Example 1, using the corresponding starting materials.

Elemental microanalysis:

|  | C % | H % |
|---|---|---|
| calculated | 67.04 | 7.40 |
| found | 66.84 | 7.38 |

EXAMPLE 22:
1-{[4-(4-Methoxybicyclo[2.2.2]oct-1-yl)phenyl]methoxy}cyclopentanecarboxylic acid, sodium salt This compound was obtained according to the procedure described in Example 1, using the corresponding starting materials.

Elemental microanalysis:

|  | C % | H % |
|---|---|---|
| calculated | 69.45 | 7.68 |
| found | 69.78 | 7.86 |

EXAMPLE 23: N-[4-(4-methoxybicyclo[2.2.2]oct-1-yl)benzoyl]glycine, sodium salt

The expected product is obtained by DCC/HOBT peptide coupling according to the technique described by W. KÖNIG and R. GEIGER (Chem. Ber., 103, 788, 2024, 1970) from the compound described in Example 9 in the form of free acid and the methyl ester of glycine, followed by a saponification in methanol/sodium hydroxide medium.

Elemental microanalysis:

|  | C % | H % | N % |
|---|---|---|---|
| calculated | 63.71 | 6.53 | 4.13 |
| found | 63.92 | 6.56 | 4.46 |

EXAMPLE 24:
2-Methyl-2-{2-[4-(4-methoxybicyclo[2.2.2]oct-1-yl)phenyl]ethoxy}propionic acid, sodium salt Stages A to G these stages are identical to Stages A to G of Example 8.

Stage H:
[4-(4-Methoxybicyclo[2.2.2]oct-1-yl)phenyl]acetic acid 50 mmol of the compound obtained in the preceding stage, 130 ml of 20% potassium hydroxide and 130 ml of ethylene glycol are refluxed for 5 hours. After filtration and cooling, the filtrate is acidified and the expected product is obtained after filtration of the precipitate, washing with water and drying.

Elemental microanalysis:

|  | C % | H % |
|---|---|---|
| calculated | 74.42 | 8.08 |
| found | 74.33 | 8.22 |

Stage I:
2-[4-(4-Methoxybicyclo[2.2.2]oct-1-yl)phenyl]ethanol 55 mmol of lithium aluminum hydride are added to 100 ml of anhydrous tetrahydrofuran, under an argon atmosphere, and then, at room temperature, dropwise, a solution containing 37 mmol of the compound obtained in the preceding stage in 300 ml of anhydrous THF. The mixture is refluxed for 3 hours. After cooling, hydrolysis with 9.4 ml of isopropanol and 5.6 ml of a saturated sodium chloride solution, the mixture is stirred overnight. The precipitate is drained, washed with THF, taken up in ethyl acetate, washed with sodium bicarbonate and then with water and finally after evaporation, filtered and dried and gives the expected product.

Stage J:
2-Methyl-2-{2-[4-(4-methoxybicyclo[2.2.2]oct-1-yl)phenyl]ethoxy}propionic acid, sodium salt 144 mmol of sodium hydroxide powder are added to a solution containing 29 mmol of the compound obtained in the preceding stage in 43 ml of anhydrous acetone. The mixture is refluxed and 3 ml of chloroform, in 8.7 ml of anhydrous acetone, are added under reflux. The reflux is maintained for 4 hours. After cooling and evaporation, the residue is taken up in a water-/ethyl acetate mixture. After acidification, the crystals formed are filtered, rinsed and dried and give the expected product after conversion to the corresponding sodium salt.

Elemental microanalysis:

|  | C % | H % |
|---|---|---|
| calculated | 68.46 | 7.93 |
| found | 68.60 | 7.68 |

EXAMPLE 25:
2-Methyl-2-{[4-(4-methoxybicyclo[2.2.2]oct-1-yl)phenyl]methylthio}propionic acid, sodium salt Stages A to F these stages are identical to Stages A to F of Example 2.

Stage G:
{([4-(4-Methoxybicyclo[2.2.2]oct-1-yl)phenyl]methylthio}methyl ketone 19.8 g of cesium carbonate, in 100 ml of anhydrous dimethylformamide and then 8.06 ml of thioacetic acid, in 50 ml of anhydrous dimethylformamide, are placed in a three-necked round-bottom flask protected from light. The mixture is stirred, at room temperature, until complete dissolution is obtained, then it is cooled on an ice-water bath. 86 mmol of the compound obtained in the preceding stage, in 60 ml of anhydrous DMF, are then added and the mixture is kept stirring overnight at room temperature. After evaporation, taking up in ethyl acetate, washing with 0.1N hydrochloric acid and then with a saturated sodium chloride solution and evaporation, the expected product is obtained by purification of the residue by silica column chromatography, using as eluent an ethyl acetate/pentane mixture (1/9).

Stage H: Ethyl 2-methyl-2-{[4-(4-methoxybicyclo-[2.2.2]oct-1-yl)phenyl]methylthio}propionate 20 mmol of the compound obtained in the preceding stage are placed, under a nitrogen atmosphere, in 50 ml of anhydrous ethanol. 46 mg of sodium are then added in portions. After leaving in contact for 15 minutes, 20 mmol of ethyl 2-bromoisobutyrate, in solution in 20 ml of anhydrous ethanol, are slowly added. The mixture is refluxed for one hour. After 2 days at room temperature, 1.1 equivalent of 1N hydrochloric acid are added. The precipitate formed is filtered, rinsed with methanol and gives the expected product.

Stage I:
2-Methyl-2-{[4-(4-methoxybicyclo[2.2.2]oct-1-yl)phenyl]methylthio}propionic acid, sodium salt The expected product is obtained according to the procedure described in Stage H of Example 1.

Elemental microanalysis:

|  | C % | H % | S % |
|---|---|---|---|
| calculated | 64.84 | 7.35 | 8.65 |
| found | 65.10 | 7.40 | 8.08 |

EXAMPLE 26:
3-Amino-6-fluoro-2-[4-(4-methoxybicyclo-[2.2.2]oct-1-yl)phenyl]quinoline-4-carboxylic acid, sodium salt

Stage A:
[4-(4-Methoxybicyclo[2.2.2]oct-1-yl)phenyl](chloromethyl) ketone 42 mmol of the acid chloride of the compound described in Example 8, in 100 ml of anhydrous THF, are cooled on an ice bath. 230 ml of a 0.32N diazomethane solution in ether are then added dropwise. The mixture is stirred for 30 minutes at 0° C. and then for 3 h 30 min at room temperature. The excess diazomethane is then expelled under a stream of nitrogen. After cooling on the ice bath, a stream of gaseous hydrochloric acid is passed for 10 minutes and then the mixture is again left for 10 minutes at 0° C. After evaporation, the expected product is obtained.

Stage B:
4-(4-Methoxybicyclo[2.2.2]oct-1-yl)phenyl](diformylamidomethyl)ketone 23 mmol of sodium diformyl amide are added to 20 mmol of the compound obtained in the preceding stage in 20 ml of acetonitrile. The mixture is refluxed for 4 hours. The expected product is then obtained after filtration and evaporation of the filtrate.

Stage C:
[4-(4-Methoxybicyclo[2.2.2]oct-1-yl)phenyl](aminomethyl)ketone, hydrochloride 15 mmol of the compound obtained in the preceding stage, in 37 ml of a hydrochloric solution of ethanol at 5%, are stirred for 6 days at room temperature. After evaporation, the expected product is obtained.

Stage D:
3-Amino-6-fluoro-2-[4-(4-methoxybicyclo-[2.2.2]oct-1-yl)phenyl]quinoline-4-carboxylic acid, sodium salt 17.4 mmol of 5-fluoroisatine are placed in 25 ml of water. 95 mmol of sodium hydroxide pellets, in 15 ml of water, are then added. The mixture is heated to 90° C. and 24 mmol of the compound obtained in the preceding stage in 80 ml of an ethanol/water mixture (1/1) are then slowly added at this temperature which is then maintained for 2 hours. After cooling, evaporation of the ethanol and filtration, the filtrate is acidified to pH 2.5 with acetic acid. The precipitate is filtered, washed with water and after conversion to the sodium salt, gives the expected product.

Mass spectrum: FAB+/[MH]+m/z=443

EXAMPLE 27:
(Z)-2-methyl-[4-(4-methoxybicyclo[2.2.2]oct-1-yl)phenyl]prop-2-enoic acid, sodium salt

Stages A to H these stages are identical to Stages A to H of Example 9.

Stage I: Ethyl 2-methyl-[4-(4-methoxybicyclo[2.2.2]oct-1-yl)phenyl]prop-2-enoate 10 mmol of $(CF_3CH_2O)_2PO-CHCH_3CO_2CH_2CH_3$ and 10 mmol of crown ether 18-crown-6 are placed in 150 ml of anhydrous THF at −78° C. 20 ml of a 0.5M potassium hexamethyldisilazane solution, and then 10 mmol of the compound obtained in the preceding stage in 50 ml of anhydrous THF are then added. The mixture is kept for 2 hours at −78° C., evaporated, and taken up in a water/ethyl acetate mixture. The organic phase is then washed, dried and evaporated and the expected product is obtained after silica column purification of the residue, using as eluent a 95/5 pentane/ethyl acetate mixture.

Stage J:
(Z)-2-methyl-[4-(4-methoxybicyclo[2.2.2]oct-1-yl)phenyl]prop-2-enoic acid, sodium salt 7 mmol of the compound obtained in the preceding stage are placed in 10 ml of methanol in the presence of 7.7 mmol of sodium hydroxide pellets and refluxed for 3 hours. After filtration, evaporation, taking-up in water, extraction with ether and evaporation, the expected product is obtained after conversion of the acid to the corresponding sodium salt.

Elemental microanalysis:

|  | C % | H % |
|---|---|---|
| calculated | 70.79 | 7.19 |
| found | 71.24 | 7.15 |

Pharmacological study of the compounds of the invention

EXAMPLE 28: Activity in vivo on the acute-phase proteins

The biological activity of the compounds of the invention was determined in particular on the plasma albumin of rats 6 days after subcutaneous injection of complete Freund's adjuvant. Negative protein of the acute phase of the inflammation, albumin, which is substantially reduced by the inflammatory state which follows the adjuvant, is completely or partially restored by the compounds administered at the daily oral dose of 100 mg/kg.

Experimental procedure

Adjuvant arthritis in rats, described for the first time by Pearson (Pearson CM., Proc. Soc. Exp. Biol. Med., 1956, 91, 95-101) was caused by injecting 0.1 ml of complete Freund's adjuvant (4 mg of Mycobacterium butyricum in suspension in 1 ml of paraffin oil/water/Tween 80) into the subplantar region of the hind legs of Lewis female rats (aged 62 days). The products were administered daily in the form of an aqueous solution or a suspension in hydroxypropyl cellulose at 0.2% according to their solubility.

Their activity on the acute-phase proteins was evaluated by determining the plasma levels of albumin 7 days after the induction of arthritis (colorimetric assay method described by Lewis (Lewis E J. et al., J. Pharmacol. Meth. 1989, 21, 183-94), the adjuvant itself causing a drop of 31% in the basal albumin level. The clinical effect was assessed by plethysmometric measurement of the volume of the hind legs and, at 14 days, by grading the overall effects of polyarthritis (red blotch and swelling of each joint, nodules at the level of the tail and the ears).

| Examples | Hypoalbuminemia correction |
|---|---|
| Example 1 | 64% |
| Example 2 | 100% |
| Example 3 | 25% |
| Example 13 | 12% |

The activity of the compound of Example 2 on this parameter is comparable to that of dexamethasone (0.25 mg/kg/d). At the same time, the products tend to reduce the intensity of the acute edema by the 6th day and prevent the severity of the polyarthritis observed 14 days after the injection of adjuvant. Accordingly, the compound of Example 2, like dexamethasone, totally inhibits (100%) the onset of polyarthritis at 14 days. The compound of Example 26, for its part, inhibits its onset by 96%. Under these conditions, romazarit inhibits the inhibition of polyarthritis by 45%.

EXAMPLE 29: Pharmaceutical composition

Preparation formula for 1000 tablets in 20 mg doses

| Compound of Example 2 | 20 g |
|---|---|

-continued

| Hydroxypropyl cellulose | 2 g |
|---|---|
| Wheat starch | 10 g |
| Magnesium stearate | 100 g |
| Talc | 3 g |

We claim:

1. A compound selected from those of formula (I):

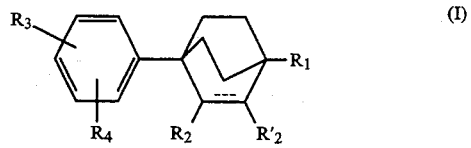

in which:

$R_1$ represents halogen, hydroxy, linear or branched ($C_1$–$C_6$) alkyl (optionally substituted by one or more halogen), linear or branched ($C_1$–$C_6$) alkoxy (optionally substituted by one or more halogen), cyano, amino (unsubstituted or substituted by one or two linear or branched ($C_1$–$C_6$) alkyl), mercapto, linear or branched ($C_1$–$C_6$) alkylthio or phenoxy (unsubstituted or substituted by one or more halogen, hydroxy, linear or branched ($C_1$–$C_6$) alkyl, linear or branched ($C_1$–$C_6$) alkoxy or linear or branched ($C_1$–$C_6$) trihaloalkyl, which are identical or different), $R_2$ and $R'_2$ represent two hydrogen in the case where the bicyclooctane ring is unsaturated, or alternatively $R_2$ or $R'_2$, in the case where the cyclooctane ring is saturated, which are identical or different, represent hydrogen or halogen, hydroxy, linear or branched ($C_1$–$C_6$) alkyl, linear or branched ($C_1$–$C_6$) alkoxy, cyano, amino (unsubstituted or substituted by one or two linear or branched ($C_1$–$C_6$) alkyl) or oxo, $R_3$ represents any one of the following groups:

—$CO_2H$ (on the condition that in this case, $R_1$ is different from halogen, linear ($C_1$–$C_6$) alkyl or amino),

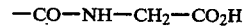

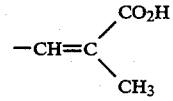

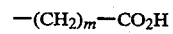

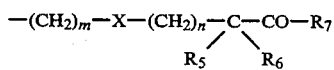

in which:

m represents 1, 2 or 3,

X represents oxygen or sulfur or N-R (in which R is hydrogen or linear or branched ($C_1$–$C_6$) alkyl), $R_5$ or $R_6$, which are identical or different, represent hydrogen, linear or branched ($C_1$–$C_6$) alkyl, trifluoromethyl or

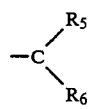

forms (C₃–C₆) cycloalkyl, n represents 0, 1 or 2,

R₇ represents hydroxy, linear or branched (C₁–C₆) alkoxy, amino (unsubstituted or substituted by one or two linear or branched (C₁–C₆) alkyl), —O—CH₂—CO—NRR' (such that R and R' represent linear or branched (C₁–C₆) alkyl, or form, with the nitrogen atom carrying them, a 5 or 6-membered heterocycle), or any one of the following heterocycles:

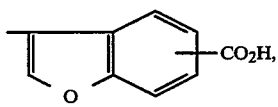

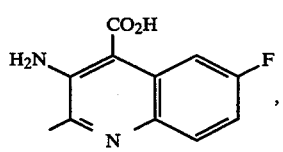

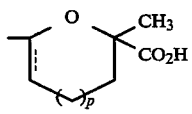

in which p is equal to 0 or 1, or

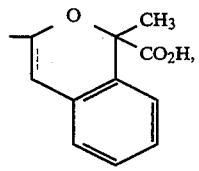

R₄ represents hydrogen or halogen or linear or branched (C₁–C₆) alkyl, linear or branched (C₁–C₆) alkoxy or (C₁–C₆) trihaloalkyl, the dotted lines in the rings indicating the presence or absence of a double bond, their enantiomers, diastereoisomers, and epimers, as well as their addition salts with a pharmaceutically acceptable acid or base.

2. A compound of claim 1, selected from those in which the bicyclooctane ring is saturated, its enantiomers, diastereoisomers and epimers, and its addition salts with a pharmaceutically-acceptable acid or base.

3. A compound of claim 1, selected from those in which R₂ and R'₂ represent two hydrogen, its enantiomers, diastereoisomers and epimers and its addition salts with a pharmaceutically-acceptable acid or base.

4. A compound of claim 1, which is selected from 2-methyl-2-{[4-(4-methoxybicyclo[2.2.2]oct-1-yl)phenyl]methoxy}propionic acid, and its addition salts with a pharmaceutically-acceptable base.

5. A method for treating an animal or human living body afflicted with a condition of arthritis or an inflammatory Phenomenon in which the acute-phase proteins become modified, comprising the step of administering to the living body an amount of a compound of claim 1 which is effective for alleviation of said condition.

6. A pharmaceutical composition useful in alleviating a condition of arthritis or an inflammatory phenomenon in which the acute-phase proteins become modified, comprising as active principle an effective amount of a compound as claimed in claim 1, together with one or more pharmaceutically-acceptable excipients or vehicles.

* * * * *

UNITED STATES PATENT AND TRADEMARK OFFICE
CERTIFICATE OF CORRECTION

PATENT NO. : 5,403,953
DATED : April 4, 1995                                Page 1 of 3
INVENTOR(S) : Guillaume de Nanteuil, et al It is certified that error appears in the above-indentified patent and that said Letters Patent is hereby corrected as shown below:

Title page, OTHER PUBLICATIONS; first occurrence "Craik, R" should read -- Craik, D --

Title page, [57] ABSTRACT; Formula in "$R_7$"; should all be on one line, namely -- $-O-CH_2-CO-NRR'$ --

Title page, [57] ABSTRACT; paragraph missing after "...NRR',"; should read -- or any one of the heterocycles as defined in the description --

Column 5, line 61; add -- (I), -- after "formula"

Column 6, line 23; "a" should be underlined

Column 6, line 48; "b" should be underlined

Column 8, line 29; add -- (I), -- to end of sentence

Column 13, line 45; add -- : -- after F (Pg 19, line 23)
Column 14, line 11 (approx.); add -- : -- after F Column 15, line 2; "[2.2.2]" should be all on same line Column 15, line 5; add -- : -- to end of line Column 15, lines 10 & 11; "[2.2.2]" should be all on same line Column 15, line 44; add -- : -- to end of line

UNITED STATES PATENT AND TRADEMARK OFFICE
CERTIFICATE OF CORRECTION

PATENT NO. : 5,403,953
DATED : April 4, 1995
INVENTOR(S) : Guillaume de Nanteuil, et al It is certified that error appears in the above-indentified patent and that said Letters Patent is hereby corrected as shown below:

Column 16, line 21; "octo" should read -- oct --

Column 17, line 68; "Elemental microanalysis:" should go at top of Column 18

Column 18, line 34; add -- : -- to end of line

Column 18, line 68; should be moved to top of Column 19

Column 20, line 5; add -- : -- to end of line

Column 20, line 66; add -- : -- to end of line

Column 21, line 55; delete "(" at end of line, keeping the dash

Column 21, line 56; add -- ( -- to beginning of line

Column 22, line 38; add -- : -- to end of line

Column 22, line 68; "Elemental microanalysis:" should go on the top of Column 23

UNITED STATES PATENT AND TRADEMARK OFFICE
CERTIFICATE OF CORRECTION

PATENT NO. : 5,403,953
DATED : April 4, 1995
INVENTOR(S) : Guillaume de Nanteuil, et al Page 3 of 3

It is certified that error appears in the above-indentified patent and that said Letters Patent is hereby corrected as shown below:

Column 26, line 16; add a "dash" between pharmaceutically acceptable"

Column 26, line 23; add -- , -- after epimers

Column 26, line 31; "P" should read -- p --

Signed and Sealed this

Eighth Day of August, 1995

Attest:

BRUCE LEHMAN

*Attesting Officer*    *Commissioner of Patents and Trademarks*